(12) United States Patent
Breitenbach et al.

(10) Patent No.: US 8,293,374 B2
(45) Date of Patent: Oct. 23, 2012

(54) TEST SYSTEM FOR EVALUATING THE COMPATIBILITY OF BIOLOGICALLY ACTIVE SUBSTANCES WITH COPOLYMERS

(75) Inventors: Joerg Breitenbach, Mannheim (DE); Bernd Liepold, Heidelberg (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 2466 days.

(21) Appl. No.: 10/508,483

(22) PCT Filed: Mar. 19, 2003

(86) PCT No.: PCT/EP03/02872
§ 371 (c)(1), (2), (4) Date: Feb. 23, 2005

(87) PCT Pub. No.: WO03/080120
PCT Pub. Date: Oct. 2, 2003

(65) Prior Publication Data
US 2005/0131054 A1    Jun. 16, 2005

(30) Foreign Application Priority Data
Mar. 25, 2002 (DE) .................. 102 13 242

(51) Int. Cl.
*B32B 27/06* (2006.01)
*A61K 9/20* (2006.01)
*G01N 21/00* (2006.01)

(52) U.S. Cl. .......... 428/480; 436/164; 424/464
(58) Field of Classification Search .......... None
See application file for complete search history.

(56) References Cited

U.S. PATENT DOCUMENTS

| | | |
|---|---|---|
| 3,389,174 A | 6/1968 | Nash et al. |
| 4,801,460 A | 1/1989 | Goertz et al. |
| 5,426,163 A * | 6/1995 | Buehler et al. ............... 526/207 |
| 5,804,263 A * | 9/1998 | Goldberg et al. ............ 428/34.7 |
| 6,497,886 B1 | 12/2002 | Breitenbach et al. |
| 6,599,931 B1 | 7/2003 | Breitenbach et al. |

FOREIGN PATENT DOCUMENTS
EP    0 987 549 A2    3/2000

OTHER PUBLICATIONS

Chiou and Riegelman, Pharmaceutical Applications of Solid Dispersion Systems, J.Pharm.Sci., vol. 60, pp. 1281-1300, Sep. 1971.

* cited by examiner

*Primary Examiner* — Yelena G Gakh
(74) *Attorney, Agent, or Firm* — Novak Druce + Quigg LLP

(57) ABSTRACT

A test solution agent, a test system and a method for evaluating the compatibility of biologically active substances with N-vinylpyrdolidone are disclosed.

9 Claims, No Drawings

TEST SYSTEM FOR EVALUATING THE COMPATIBILITY OF BIOLOGICALLY ACTIVE SUBSTANCES WITH COPOLYMERS

The present invention relates to a liquid mixture serving as test solvent, and to a test system and a method for evaluating the compatibility of biologically active substances with N-vinylpyrrolidone copolymers using the liquid mixture.

Solid dispersions, i.e. homogeneous microdisperse phases of two or more solids and the special case of so-called solid solutions (molecular dispersion systems), and their use in pharmaceutical technology are generally known, cf. Chiou and Riegelman J. Pharm. Sci., 60, 1281-1300 (1997).

Solid solutions can be produced by melting processes or by the solution process. Particularly suitable as polymeric excipient for producing such solid dispersions or solid solutions are N-vinylpyrrolidone copolymers, i.e. copolymers of N-vinylpyrrolidone with further ethylenically unsaturated monomers. Solid solutions of biologically active substances based on such copolymers can be produced particularly advantageously by melt extrusion as described, for example, in EP-A 240 904.

However, there are minimum requirements on the amounts employed to produce melt extrudates. If only relatively small amounts of active ingredient are available, it cannot be predicted with certainty whether an active ingredient will form a solid solution together with the chosen copolymer. However, it is precisely when drug products based on new active ingredients are being developed that only relatively small amounts of the active ingredient are frequently available, so that the possibility of prediction with the aid of a simple test system appears to be extremely desirable.

It is likewise desirable to be able to make predictions concerning the stability of solid solutions or solid dispersions. This is because, depending on the compatibility of the active ingredient with the copolymer, the previously homogeneous disperse phase may become inhomogeneous, or the active ingredient may recrystallize. Such phase separation or recrystallization is unwanted because of the change in the homogeneity and the release characteristics associated therewith.

EP-A 0987549 discloses a test system for characterizing the compatibility of biologically active substances with polyvinylpyrrolidone in a solid dispersion.

It is the object of the present invention to indicate a test system with the aid of which it is possible to predict the compatibility of biologically active substances and N-vinylpyrrolidone copolymers in a simple manner.

It has surprisingly been found that the dissolving properties of N-vinylpyrrolidone copolymers can be simulated by a liquid mixture of 1,3-bis(pyrrolidon-1-yl)butane with certain compounds which have structural similarity to the comonomer units present in the copolymer.

The invention therefore relates to a liquid mixture which comprises
a) 1,3-bis(pyrrolidon-1-yl)butane and
b) at least one compound of the formula I

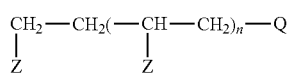

in which
Q is $CH_2$—Z, $CH_2$—$CH_2$—Z or CHZ—$C_1$-$C_4$-alkyl,
n is 0, 1, 2 or 3, and the Z radicals are $C_1$-$C_{20}$-alkylcarbonyloxy, carboxyl, $C_1$-$C_{20}$-alkyloxycarbonyl, $C_2$-$C_4$-hydroxyalkyloxycarbonyl, di($C_1$-$C_4$-alkyl)amino-$C_2$-$C_4$-alkyloxycarbonyl or tri ($C_1$-$C_4$-alkyl) ammonium-$C_2$-$C_4$-alkyloxycarbonyl.

All the Z radicals occurring in formula I are preferably identical. "Liquid mixture" is intended for the purposes of the present application to mean that the mixture is in liquid form at least at slightly elevated temperature, e.g. at 45° C., preferably even at room temperature.

The liquid mixture serves as test solvent which simulates the dissolving, properties of the N-vinyl-pyrrolidone copolymer. The liquid mixture normally contains components a) and b) in a ratio of from 10:1 to 1:10, preferably 5:1 to 1:5, by weight.

The invention additionally relates to a test system for evaluating the compatibility of a biologically active substance with a copolymer which includes units of N-vinylpyrrolidone and of at least one ethylenic unsaturated monomer of the formula II $$CH_2=CR-Z'$$ (II)

in which R is hydrogen or methyl, and Z' has the meaning indicated above for Z, where the test system includes the liquid mixture defined above and at least one biologically active substance.

The invention additionally relates to a method for evaluating the compatibility of a biologically active substance with an N-vinylpyrrolidone copolymer, where the copolymer includes units of N-vinylpyrrolidone in a proportion by weight of xvp and units of at least one ethylenically unsaturated monomer of the formula II $$CH_2=CR-Z'$$ (II)

in which R is hydrogen or methyl, Z' is $C_1$-$C_{20}$-alkyl-carbonyloxy, carboxyl, $C_1$-$C_{20}$-alkyloxycarbonyl, $C_2$-$C_4$-hydroxyalkyloxycarbonyl, di($C_1$-$C_4$-alkyl)amino-$C_2$-$C_4$-alkyloxycarbonyl or tri($C_1$-$C_4$-alkyl) ammonium-$C_2$-$C_4$-alkyloxycarbonyl, in a proportion by weight of $x_M$, in which
a) a test solvent which comprises 1,3-bis(pyrrolidon-1-yl) butane in a proportion by weight of $x_{VP}$ and a compound of the formula I in a proportion by weight of $x_M$

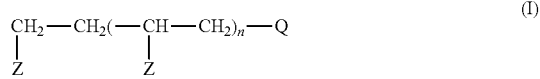

in which Q is $CH_2$—Z, $CH_2$—$CH_2$—Z or CHZ—$C_1$-$C_4$-alkyl, n is 0, 1, 2 or 3, the Z radicals are identical and correspond to the Z' radical, is prepared,
b) the biologically active substance is brought into contact with the test solvent, and
c) the phase behavior of the mixture and/or solubility of the biologically active substance in the test solvent is determined.

$X_{VP}$ is in general from 10 to 90% by weight, usually 30 to 70% by weight. $x_M$ is in general from 90 to 10% by weight, usually 70 to 30% by weight. If more than one monomer of the formula II is present, the individual contribution of the various monomers $x_{M1}$, $x_{M2}$, . . . are to be put for $x_M$.

The radicals Z and Z' are preferably $C_1$-$C_4$-alkyl-carbonyloxy, carboxyl, $C_1$-$C_4$-alkyloxycarbonyl or $C_2$-$C_4$-hydroxyalkyloxycarbonyl. If Z or Z' are tri($C_1$-$C_4$-alkyl) ammonium-$C_2$-$C_4$-alkyloxycarbonyl, they are accompanied by one equivalent of a pharmaceutically acceptable anion such as hydroxide, sulfate, hydrogen-sulfate, carbonate, hydrogen-carbonate, a halide, in particular chloride, the anion of an organic acid such as acetate, lactate, fumarate, or the like. If Z or Z' are carboxyl, the carboxyl group may also be wholly or partly neutralized, in which case suitable charge-balancing cations are pharmaceutically acceptable cations such as alkali metal or alkaline earth metal ions, e.g. sodium or potassium, or unsubstituted or substituted ammonium ions such as dimethylammonium, trimethylammonium, diethanolammonium and the like.

1,3-Bis(pyrrolidon-1-yl)butane can be obtained by dimerization of N-vinylpyrrolidone under acidic reaction conditions and subsequent hydrogenation of the resulting 1,3-bis (pyrrolidon-1-yl)butene to 1,3-bis-(pyrrolidon-1-yl)butane (cf. Breitenbach et al., Naturwissenschaften 42, 955, 155; 440). 1,3-Bis-(pyrrolidon-1-yl)butane is a colorless oily liquid with a boiling point of 205 to 215° C. (0.2 mbar).

The compounds of the general formula I are either commercially available or can be prepared in a simple manner. Use for example of 1,3-diacetoxybutane and, in particular, 1,4-diacetoxybutane as compound of the formula I has been successful. Compounds of the formula I can be obtained for example by esterification of polyols such as 1,3-butanediol, 1,4-butanediol or 1,3,5-pentanetriol with carboxylic acids such as acetic acid or derivatives thereof or by esterification of polycarboxylic acids such as glutaric acid or adipic acid with suitable alcohols.

Suitable copolymers whose compatibility with biologically active substances can be evaluated with the aid of the test system of the invention are copolymers of N-vinylpyrrolidone with ethylenically unsaturated monomers of the formula II

$$CH_2 = CR - Z' \quad (II)$$

in which R is hydrogen or methyl, and Z' is $C_1$-$C_{20}$-alkylcarbonyloxy, carboxyl, $C_1$-$C_{20}$-alkyloxycarbonyl, $C_2$-$C_4$-hydroxyalkyloxycarbonyl, di($C_1$-$C_4$-alkyl)amino-$C_2$-$C_4$-alkyloxycarbonyl or tri($C_1$-$C_4$-alkyl)ammonium-$C_2$-$C_4$-alkyloxycarbonyl.

Monomers of the formula II which may be mentioned are vinyl esters of $C_1$-$C_{20}$-alkanecarboxylic acids, such as vinyl acetate or vinyl propionate, acrylic or methacrylic acid, $C_1$-$C_{20}$-alkyl esters of acrylic acid or methacrylic acid, such as methyl acrylate, methyl methacrylate, ethyl acrylate, ethyl methacrylate, $C_2$-$C_4$-hydroxyalkyl(meth)acrylates such as hydroxyethyl acrylate, di($C_1$-$C_4$-alkyl)amino-$C_2$-$C_4$-alkyl (meth)-acrylates such as dimethylaminopropyl acrylate, or (meth)acryloyloxy-$C_2$-$C_4$-alkyltri($C_1$-$C_4$-alkyl)ammonium salts such as acryloyloxypropyltrimethylammonium chloride.

The preferred copolymers include those of N-vinyl-pyrrolidone and vinyl acetate, especially in a ratio of 70:30 to 30:70 by weight; and copolymers of N-vinyl-pyrrolidone with methyl methacrylate, especially in a ratio of from 20:80 to 55:45 by weight.

The copolymers generally have a Fikentscher K value of from 10 to 110, in particular from 20 to 80.

The radical Z in the compound of the formula I is chosen in accordance with the radical Z' in the comonomer of the copolymer to be simulated. Thus, for example, a mixture of 1,3-bis(pyrrolidon-1-yl)butane with 1,4-diacetoxybutane serves to simulate the dissolving properties of N-vinylpyrrolidone/vinyl acetate copolymers. It is, of course, possible for the copolymer to be simulated also to contain two or more different monomers of the formula II. The test solvent is then prepared by using two or more different compounds of the formula I with appropriately chosen radicals Z as component b).

Compatibility means for the purposes of the present application the ability of a substance to form with the N-vinylpyrrolidone copolymer a homogeneous, stable solid dispersion, this solid dispersion being in particular a solid solution, i.e. a molecular dispersion of the components in one another. The test system is suitable in principle for all active pharmaceutical ingredients, crop protection agents, food supplements or cosmetic active ingredients. It is also possible to investigate detergents or dyes for their compatibility with the copolymers. The influence of formulation aids which are not themselves biologically active, such as sugars, sugar alcohols, solubilizers such as surfactants, or other polymeric aids, can also be investigated.

The method of the invention is carried out by first preparing a test solvent. The test solvent comprises 1,3-bis(pyrrolidon-1-yl)butane and a compound of the formula I in a ratio by weight which corresponds to that of N-vinylpyrrolidone and comonomer(s) in the copolymer to be simulated. The solubility of the biologically active substance to be investigated in the liquid mixture is then assessed at a defined temperature, usually room temperature. The solubility can be determined quantitatively, e.g. in % by weight based on the weight of test solvent and biologically active substance. In many cases, it is sufficient to state whether the solubility is greater or less than a particular value. For this purpose, a predetermined amount of the biologically active substance is brought into contact with the test solvent. The quantitative ratios can in principle be chosen freely. However, it is advisable to choose the concentration ranges in the test system such that they correspond to the active ingredient content typical of extrudate forms, i.e. generally from 0.1 to 70% by weight, preferably 10 to 30% by weight, of biologically active substance, based on the total weight of the test system.

The biologically active substance is normally weighed out, mixed with the test solvent and preferably blended, e.g. stirred with a laboratory magnetic stirrer at from 5 to 2000 rpm, or treated with ultrasound or a vortex homogenizer. Dissolving can also be speeded up by heating the test system. The heating preferably takes place in such a way that the heating rate approximately corresponds to that in a melt formulation, i.e. at from 0.5 to 5° C./min. The test system is preferably heated to a maximum of 140° C., e.g. to a temperature in the range from 45 to 140° C. or 110 to 140° C. However, heating to the boiling point of the liquid mixture is also possible in the individual case. The test system is then allowed to cool to the determination temperature, usually room temperature.

The phase behavior of the mixture is then assessed, i.e. it is established by visual, spectroscopic and/or thermoanalytical investigation of the resulting mixture whether the biologically active substance is able to form a homogeneous phase with the liquid mixture.

Visual inspection takes place for example using a microscope such as a usual optical microscope. It is established in this case whether a clear solution has formed. Besides visual inspection, also suitable is a spectroscopic investigation of the test system. For example, the test system can be investigated for its amorphous character with the aid of confocal Raman spectroscopy. Also suitable is the method of differential scanning calorimetry. It is possible to conclude from the presence of a homogeneous phase that the solubility of the biologically active substance is greater than the concentration of the substance in the dissolving test. Conversely, a lower solubility can be concluded from the occurrence of a phase separation.

Quantitative determination of the solubility is possible for example in the following way:

a) A concentration series is prepared by bringing various amounts of biologically active substance into contact with a constant amount of test solvent in parallel tests. After an equilibration time over a defined period at a given temperature, preferably with blending, e.g. stirring for 24 hours or ultrasound treatment for 30 min, the maximum concentration at which clear solutions are obtained is found. The solubility of the biologically active substance is between the concentration at which a clear solution is obtained but at the next concentration no clear solution is obtained.

b) An amount of the test solvent which is insufficient for completely dissolving is added to an amount of the biologically active substance, or further amounts of biologically active substance are added to the solution until the added amount no longer completely dissolves. After an equilibration time over a defined period at a given temperature, preferably with blending, e.g. stirring for 24 hours or ultrasound treatment for 30 min, a sample of the clear supernatant is taken. The mixture can for this purpose be previously centrifuged, e.g. using an ultracentrifuge at 8000 to 12 000 rpm. The concentration of the biologically active substance is determined in the sample of the clear supernatant, e.g. by high pressure liquid chromatography (HPLC). The value which is found corresponds to the solubility of the biologically active substance.

It is possible by means of the methods mentioned above to determine, depending on the equilibration conditions, the thermodynamic saturation solubility or the maximum (kinetic) solubility.

The solubility found after 24 hours at room temperature (22° C.±2° C.) essentially corresponds to the thermo-dynamic saturation solubility of the biologically active substance. This value of the solubility is a measure of the thermodynamic saturation solubility of the biologically active substance in the matrix of the copolymer at room temperature. Solid solutions of biologically active substances are thermodynamically stable if the active ingredient loading is below the thermodynamic saturation solubility of the biologically active substance in the matrix.

However, the active ingredient loading in solid solutions can be increased greatly by energy input. The maximum active ingredient loading achievable in a given matrix of a copolymer can be predicted with the test system of the invention by determining the solubility of the biologically active substance in accordance with one of the aforementioned methods a) or b), the equilibration being carried out by heating to a temperature of, for example, 140° C., in particular from 110 to 140° C., or by sonication.

The test system of the invention also allows the recrystallization behavior to be predicted. Especially for test systems in which higher active ingredient loadings than the thermodynamic saturation solubility have been set up by energy input, e.g. heating or sonication, the recrystallization behavior after the energy input ceases or after cooling to room temperature represents an important criterion. Test systems in which the biologically active substance does not recrystallize immediately are investigated for long-term stability. It is possible to use the following conditions for this, for example:

leaving to stand at room temperature for 24 hours,
storage for one month, 3 months, 6 months in climate zone 2 (25° C., 60% relative humidity) or climate zone 4 (20° C., 70% relative humidity), or
stress storage at 40° C., 75% relative humidity for up to 6 months.

It is also possible with the aid of the test system of the invention to investigate the influence of excipients or a solubility-increasing or solubility-reducing effect of the presence of a second or further biologically active substance on the solubility of a first biologically active substance in the matrix of the copolymer. For this purpose, these excipients, e.g. solubilizers, or further biologically active substances are added to the test solvent in addition to the biologically active substance to be tested. It is then possible again to determine the thermodynamic saturation solubility and/or the maximum solubility as indicated above.

The invention is illustrated in more detail by the following examples.

EXAMPLE 1

Thermodynamic Saturation Solubility of Lopinavir in a Matrix of a Copolymer of N-vinyl-pyrrolidone and vinyl acetate (60:40)

The copolymer was simulated by a mixture of 1,3-bis-(pyrrolidon-1-yl)butane and 1,4-diacetoxybutane in the ratio of 6:4 by weight.

Method a)

In parallel tests, the active ingredient was weighed into glass bottles and made up with the test solvent appropriate for the concentrations indicated in the table below (all concentrations in weight/weight). All seven samples were provided with a magnetic stirring bar and stirred at room temperature for 24 hours. It was established by visual inspection that the active ingredient formed clear solutions up to 24.1%; the test with 26.0% showed incomplete dissolving. The saturation solubility was therefore between 24.1 and 26.0% by weight.

| Lopinavir [%] | 20.2 | 21.9 | 24.1 | 26.0 | 29.5 | 33.9 | 36.3 |
|---|---|---|---|---|---|---|---|
| Clear solution | + | + | + | − | − | − | − |

Method b)

In an alternative determination method, 150 mg of lopinavir were mixed with 350 mg of the test solvent and stirred at room temperature for 24 hours. The sample was then centrifuged at 12 000 rpm for one minute. The clear supernatant was investigated by HPLC. A solubility of 24.9% by weight was found.

Method c)

The maximum solubility was determined by mixing 60 mg of lopinavir with 140 mg of the test solvent and treating with ultrasound at room temperature for 30 min. The solvent was then centrifuged at 10 000 rpm for 10 min. A sample of the clear supernatant was investigated by HPLC. A maximum solubility of 39.72% by weight was found. The remaining amount of the sample was stored at room temperature for 4 weeks. Then a further sample of the supernatant was taken and investigated by HPLC. A concentration of 28.87% by weight was found.

EXAMPLE 2

Thermodynamic Saturation Solubility of Lopinavir under the Influence of polyoxyethylene-glycerol trihydroxystearate (Cremophor RH 40®)

Example 1a) was repeated but with use of the concentrations indicated in the table below, and with the test solvent containing 5% by weight Cremophor RH 40. The saturation solubility was found to be between 22.0 and 26.0%.

| Lopinavir [%] | 20.0 | 22.0 | 23.7 | 26.0 | 30.0 | 33.0 | 35.8 |
|---|---|---|---|---|---|---|---|
| Cremophor [%]* | 5 | 5 | 5 | 5 | 5 | 5 | 5 |
| Clear solution | + | + | + | − | − | − | − |

*based on the test solvent

Example 1b) was repeated but with the test solvent containing 5% by weight Cremophor RH 40. A solubility of 22.8% was found.

It was possible to show with the aid of the test system of the invention that Cremophor RH 40 reduces the thermodynamic saturation solubility of lopinavir.

EXAMPLE 3

Thermodynamic Saturation Solubility of Lopinavir under the Influence of Ritonavir An active ingredient premix of the two abovementioned active ingredients in a ratio of 4:1 by weight was prepared. Example 1a) was repeated with this active ingredient mixture, the concentration being as in the table below.

| Lopinavir [%] | 19.2 | 20.6 | 23.9 | 27.8 |
|---|---|---|---|---|
| Ritonavir [%] | 4.8 | 5.2 | 6 | 6.9 |
| Total active ingredient [%] | 24.0 | 25.8 | 29.9 | 34.7 |
| Clear solution | + | + | − | − |

Example 1b) was repeated with the abovementioned active ingredient premix. 21.3% by weight lopinavir was found in the clear supernatant by HPLC. It was possible with the aid of the test system of the invention to show that the presence of ritonavir reduces the thermodynamic saturation solubility of lopinavir.

EXAMPLE 4

Thermodynamic Saturation Solubility of Lopinavir under the Influence of Ritonavir and Cremophor RH 40

Example 3a) was repeated, using the concentrations indicated in the table below, and with the test solvent containing 10% by weight Cremophor RH 40. Visual determination of the concentration series led to a thermodynamic saturation solubility for the active ingredient mixture of between 23.6% and 28.0%. The HPLC method led to a result of 21.7% for lopinavir.

| Lopinavir [%] | 14.2 | 15.8 | 18.9 | 22.4 |
|---|---|---|---|---|
| Ritonavir [%] | 3.6 | 4.0 | 4.7 | 5.6 |
| Total active ingredient [%] | 17.8 | 19.8 | 23.6 | 28.0 |
| Cremophor [%]* | 10 | 10 | 10 | 10 |
| Clear solution | + | + | + | − |

*based on the test solvent

EXAMPLE 5

Melt Extrusion

A formulation containing 18.7 parts by weight of lopinavir, 4.7 parts by weight of ritonavir, 10.0 parts by weight of Cremophor RH 40 and 100 parts by weight of N-vinylpyrrolidone/vinyl acetate copolymer (60:40) was prepared for the melt extrusion. Melt extrusion of this formulation using a heated twin screw extruder resulted in stable solid solutions. After storage of the extrudates at room temperature for 8 months they underwent X-ray investigation. Both active ingredients were in X-ray amorphous form, i.e. no recrystallization of an active ingredient took place. In accordance with the prediction of the test system, a stable solid solution of the active ingredients is present.

The invention claimed is:

1. A liquid mixture comprising
   a) 1,3-bis(pyrrolidon-1-yl)butane and
   b) at least one compound of the formula I

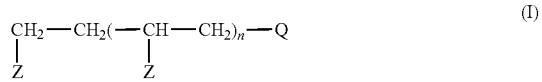

in which
Q is $CH_2$—Z, $CH_2$—$CH_2$—Z or CHZ—$C_1$-$C_4$-alkyl,
n is 0, 1, 2 or 3, and
the Z radicals are $C_1$-$C_{20}$-alkylcarbonyloxy, carboxy, $C_1$-$C_{20}$-alkyloxycarbonyl, $C_2$-$C_4$-hydroxyalkyloxycarbonyl, di($C_1$-$C_4$-alkyl)amino-$C_2$-$C_4$-alkyloxycarbonyl or tri($C_1$-$C_4$-al-kyl)ammonium-$C_2$-$C_4$-alkyloxycarbonyl.

2. The mixture as claimed in claim 1, where component b) is 1,4-diacetoxybutane.

3. The mixture as claimed in claim 1, in which components a) and b) are present in a ratio of from 10:1 to 1:10 by weight.

4. A test system for evaluating the compatibility of a biologically active substance with a copolymer which includes units of N-vinyl-pyrrolidone and of at least one ethylenic unsaturated monomer of the formula II

in which R is hydrogen or methyl, and Z' has the meaning indicated in claim 1 for Z, where the test system includes a liquid mixture as claimed in claim 1 and at least one biologically active substance.

5. The test system as claimed in claim 4, comprising from 10 to 70% by weight of biologically active substance.

6. The test system as claimed in claim 4, additionally comprising at least one formulation aid.

7. A method for evaluating the compatibility of a biologically active substance with an N-vinylpyrrolidone copolymer which includes units of N-vinylpyrrolidone in a proportion by weight of $X_{VP}$ and units of at least one ethylenically unsaturated monomer of the formula II

in which R is hydrogen or methyl, Z' is $C_1$-$C_{20}$-alkylcarbonyloxy, carboxyl, $C_1$-$C_{20}$-alkyloxycarbonyl, $C_2$-$C_4$-hydroxyalkyloxycarbonyl, di($C_1$-$C_4$-alkyl)amino-$C_2$-$C_4$-alkyloxycarbonyl or tri($C_1$-$C_4$-alkyl)ammonium-$C_2$-$C_4$-alkyloxycarbonyl, in a proportion by weight of $X_M$, in which a) a test solvent which comprises 1,3-bis-(pyrrolidon-1-yl) butane in a proportion by weight of $X_{vp}$ and a compound of the formula I in a proportion by weight of $X_M$

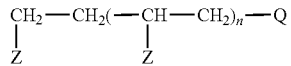 (I)

in which Q is $CH_2$—Z, $CH_2$—$CH_2$—Z or CHZ—$C_1$-$C_4$-alkyl, n is 0, 1, 2 or 3, the Z radicals are identical and correspond to the Z' radical, is prepared, b) the biologically active substance is brought into contact with the test solvent, and c) the phase behavior of the mixture and/or solubility of the biologically active substance in the test solvent is determined.

8. The method as claimed in claim 7, in which the phase behavior of the mixture is investigated visually, spectroscopically and/or thermoanalytically.

9. The method as claimed in claim 7, in which the mixture of biologically active substance and test solvent is heated to a temperature of up to 140° C.

* * * * *